US009566056B2

(12) United States Patent  
Curtis et al.

(10) Patent No.: US 9,566,056 B2  
(45) Date of Patent: Feb. 14, 2017

(54) APPARATUS AND METHOD FOR SECURING TISSUE TO BONE USING SUTURE ANCHORS WITH A PRE-LOADED PIERCING STRUCTURE AND SUTURES

(71) Applicant: AEVUMED, INC., Wayne, PA (US)

(72) Inventors: Miles Ole Curtis, Philadelphia, PA (US); Saif Khalil, Wayne, PA (US)

(73) Assignee: Aevumed, Inc., Wayne, PA (US)

( * ) Notice: Subject to any disclaimer, the term of this patent is extended or adjusted under 35 U.S.C. 154(b) by 174 days.

(21) Appl. No.: 14/072,417

(22) Filed: Nov. 5, 2013

(65) Prior Publication Data

US 2015/0127048 A1    May 7, 2015

(51) Int. Cl.
*A61B 17/04* (2006.01)
*A61B 17/06* (2006.01)
*A61B 17/00* (2006.01)

(52) U.S. Cl.
CPC ........... *A61B 17/0401* (2013.01); *A61B 17/06* (2013.01); *A61B 2017/00477* (2013.01); *A61B 2017/044* (2013.01); *A61B 2017/0458* (2013.01)

(58) Field of Classification Search
CPC .................. A61B 17/0401; A61B 2017/0445; A61B 2017/0464; A61B 17/0409; A61B 2017/0412; A61B 2017/0414; A61B 2017/0417; A61B 2017/042; A61B 2017/0422; A61B 2017/0424; A61B 2017/0425; A61B 2017/0427; A61B 2017/0429; A61B 2017/043; A61B 2017/0432; A61B 2017/0433; A61B 2017/0435; A61B 2017/0437; A61B 2017/0438; A61B 2017/044; A61B 2017/0441; A61B 2017/0443; A61B 2017/0446; A61B 2017/0448; A61B 2017/045; A61B 2017/0451; A61B 2017/0453; A61B 2017/0454; A61B 2017/0456; A61B 2017/0458; A61B 2017/0459; A61B 2017/0461; A61B 2017/0462; A61B 2017/04; A61B 2017/64; A61F 2/08; A61F 2/0811; A61F 2002/0823; A61F 2002/0847; A61F 2002/0817; A61F 2002/0829; A61F 2002/0835; A61F 2002/0841; A61F 2002/0852; A61F 2002/0858; A61F 2002/0864; A61F 2002/087; A61F 2002/0876; A61F 2002/0882; A61F 2002/0888

See application file for complete search history.

(56) References Cited

U.S. PATENT DOCUMENTS 5,258,016 A    11/1993 DiPoto et al.
5,573,548 A    11/1996 Nazre et al.
(Continued)

FOREIGN PATENT DOCUMENTS

WO    2012/129388    9/2012

OTHER PUBLICATIONS

Contact. Dictionary.com. Dictionary.com Unabridged. Random House, Inc. http://dictionary.reference.com/browse/contact (accessed: Feb. 17, 2016).*

*Primary Examiner* — Jonathan Miles
*Assistant Examiner* — Kankindi Rwego
(74) *Attorney, Agent, or Firm* — Riverside Law LLP

(57) ABSTRACT

A suture anchor is described. The suture anchor includes an elongate anchor body having a proximal end and a distal end, at least one suture secured within the anchor body, and at least one piercing structure secured within the body extending proximally out of the proximal end of the body, wherein the at least one piercing structure is engaged with
(Continued)

the at least one suture. A method of attaching soft tissue to bone in a subject is also described. The method includes the steps of securing an anchor device into a bore formed in the bone, the anchor device comprising an anchor body and at least one pre-loaded piercing structure with at least one suture attached to both the anchor body and the piercing structure, piercing a soft tissue by forcing the at least one piercing structure through the soft tissue, such that at least a portion of the at least one suture passes through the soft tissue, and tying the at least one suture against the soft tissue to secure the soft tissue to the bone.

7 Claims, 7 Drawing Sheets

(56) References Cited

U.S. PATENT DOCUMENTS

| | | | |
|---|---|---|---|
| 5,601,557 A | 2/1997 | Hayhurst | |
| 5,618,314 A | 4/1997 | Harwin et al. | |
| 5,647,874 A | 7/1997 | Hayhurst | |
| 5,697,950 A | 12/1997 | Fucci et al. | |
| 5,944,724 A * | 8/1999 | Lizardi | A61B 17/0401 606/104 |
| 5,993,459 A | 11/1999 | Larsen et al. | |
| 6,436,124 B1 | 8/2002 | Anderson et al. | |
| 6,527,795 B1 * | 3/2003 | Lizardi | A61B 17/0401 606/232 |
| 6,656,182 B1 | 12/2003 | Hayhurst | |
| 7,828,820 B2 * | 11/2010 | Stone | A61B 17/0401 606/232 |
| 7,875,042 B2 | 1/2011 | Martin et al. | |
| 7,883,529 B2 | 2/2011 | Sinnott et al. | |
| 8,267,963 B2 | 9/2012 | Williams | |
| 2009/0171400 A1 * | 7/2009 | van der Burg | A61B 17/0401 606/300 |
| 2010/0268274 A1 | 10/2010 | Williams | |
| 2011/0071551 A1 | 3/2011 | Singhatat et al. | |
| 2012/0083837 A1 * | 4/2012 | Ferragamo | A61B 17/0401 606/224 |
| 2013/0238024 A1 | 9/2013 | Taylor et al. | |

* cited by examiner

APPARATUS AND METHOD FOR SECURING TISSUE TO BONE USING SUTURE ANCHORS WITH A PRE-LOADED PIERCING STRUCTURE AND SUTURES

BACKGROUND OF THE INVENTION

The attachment of soft tissue to bone remains an important part of the practice of orthopedic surgery. The surgeon's armamentarium for attaching ligaments, tendons, or other tissues to bone includes pullout suture techniques, keyhole techniques, smooth or barbed soft tissue staples, and fixation with screws and washers. Each of these devices and techniques has advantages and disadvantages, depending on the surgical situation and the clinical application. The development of suture anchors, which has revolutionized soft tissue fixation to bone, has paralleled the development of arthroscopic surgical techniques. Suture anchors have been used successfully for rotator cuff repairs, shoulder reconstructions for instability, the repair of biceps anchor lesions (e.g., superior labrum anterior posterior (SLAP) lesions), and biceps tenodesis. The continuing evolution of suture anchors has produced a variety of types, such as absorbable, non-absorbable, screw-in, hooked, and knotless anchors and tacks, as well as those that lock into the bone on insertion.

Traditionally, the suture attachment to the soft tissue is secured via a knot made in the suture. In order to convey this type of procedure, a number of steps are required to complete this process. This process is as follows; 1) the bone is bored out and the suture anchor is deployed and secured in to the bone; 2) a surgical instrument or device such as a lasso is inserted through a second surgical port and pierces through the soft tissue; 3) a looped end wire is pushed out of the tip of the surgical instrument or device; 4) the looped end wire is then pulled out of the first suture anchor insertion port using a grasper; 5) one of the sutures is passed through the looped end wire out of the first suture anchor insertion port; 6) the looped end wire is then pulled back out of the second surgical port and sequentially pulls the suture out of the second surgical port; 7) a grasper is then inserted through the first suture anchor insertion port and pulls the suture back out of the first suture anchor insertion port; and 8) the two suture ends are then tied out of the first suture anchor insertion port and pushed down to secure the soft tissue to bone.

However, there is a clinical need for reducing the number of steps and operating time in soft tissue fixation to bone. Unfortunately, existing designs require too many steps, have relatively long operating times, and require a surgical instrument or device such as a lasso to pass a suture end through soft tissue.

For example, U.S. Pat. No. 5,697,950 describes a method and apparatus for facilitating use of a threaded suture anchor in combination with a cannulated anchor driver. The device enables a suture anchor to be preassembled with a suture so that a user need not assemble a suture anchor with suture immediately prior to use. Similarly, U.S. Pat. No. 5,993,459 describes a method and suture anchor installation system that includes a suture anchor, a loading unit, and a suture anchor installation tool. However, these methods require the use of an external instrument to pass the suture through tissue.

U.S. Pat. No. 7,875,042 describes a suture anchor loader comprises a housing with a port. On the other hand, U.S. Patent Application Publication No. 2010/0268274 describes a suture anchor member manual loading device that may include a body comprising first and second portions preventing the operator contact with a tip of a needle. In addition, U.S. Patent Application Publication No. 2011/0071551 describes a soft tissue repair system that includes a sheath, and an actuator. However, all these methods still require the use of an external instrument to pass the suture through tissue. This greatly increases the time, complexity, and risk during the fixation procedure.

Thus, there is a need in the art for an improved device and method for attachment of soft tissue to bone, which reduces the number of steps required for effective fixation. The present invention satisfies this unmet need.

SUMMARY OF THE INVENTION

The present invention includes a suture anchor comprising an elongate anchor body having a proximal end and a distal end, at least one suture secured to the anchor body, and at least one piercing structure secured within the body extending proximally out of the proximal end of the body, where the at least one piercing structure is engaged with the at least one suture.

In one embodiment, the anchor body is threaded. In one embodiment, the anchor body comprises at least one interference fit structure.

In one embodiment, the at least one piercing structure is releasably secured within the anchor body. In one embodiment, the at least one suture is releasably secured to the anchor body.

In one embodiment, the at least one piercing structure is positioned near a perimeter of the proximal end of the anchor body.

In one embodiment, the anchor body comprises a structure for engagement with an installation tool. In one embodiment, the at least one piercing structure is configured to engage an installation tool.

In one embodiment, the one or more sutures are held in the anchor body within at least one suture channel leading to a cavity formed in the anchor body. In one embodiment, the at least one suture are secured to an eyelet of the anchor body. In one embodiment, the at least one piercing structure comprises at least one hole through which a portion the at least one suture passes through.

The present invention includes a method of attaching soft tissue to bone in a subject. The method comprises securing a suture anchor into the bone, the suture anchor comprising an anchor body, at least one piercing structure, and at least one suture, wherein the at least one suture is secured to the anchor body and engages the at least one piercing structure. The method further comprises piercing a soft tissue by forcing the at least one piercing structure through the soft tissue, such that at least a portion of the at least one suture passes through the soft tissue; and tying the at least one suture against the soft tissue to secure the soft tissue to the bone.

In one embodiment, the suture anchor is secured into the bone through self-drilling. In one embodiment, the suture anchor is secured into the bone by forming a bore in the bone using a bore-forming tool, and securing the suture anchor into the bore.

In one embodiment, the soft tissue is tendon, muscle, or ligament.

In one embodiment, the suture anchor is secured into the bone using an installation tool which engages a structure of the anchor body. In one embodiment, the suture anchor is secured into the bone using an installation tool which engages the at least one piercing structure.

In one embodiment, the method further comprises releasing at least one suture from the at least one piercing structure; lifting the soft tissue off of the anchor body; and piercing a second portion of the soft tissue by forcing the at least one piercing structure through the second region of the soft tissue. In one embodiment, the method further comprises releasing the at least one piercing structure from the anchor body.

The present invention also includes a system for attaching soft tissue to bone in a subject. The system comprises a suture anchor and an installation tool. The suture anchor of the system comprises an elongate anchor body having a proximal end and a distal end, at least one suture secured to the anchor body, and at least one piercing structure secured within the body extending proximally out of the proximal end of the body, where the at least one piercing structure is engaged with the at least one suture.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIGS. 4A and 4B, is a cross-sectional view of the exemplary bone anchor body without a pre-loaded needle (FIG. 4A) and with a pre-loaded needle and suture (FIG. 4B) of FIG. 1.

FIGS. 5A-5C, is a set of perspective views of alternative embodiments for securing the suture to the anchor body.

DETAILED DESCRIPTION

Definitions

Figure 1:
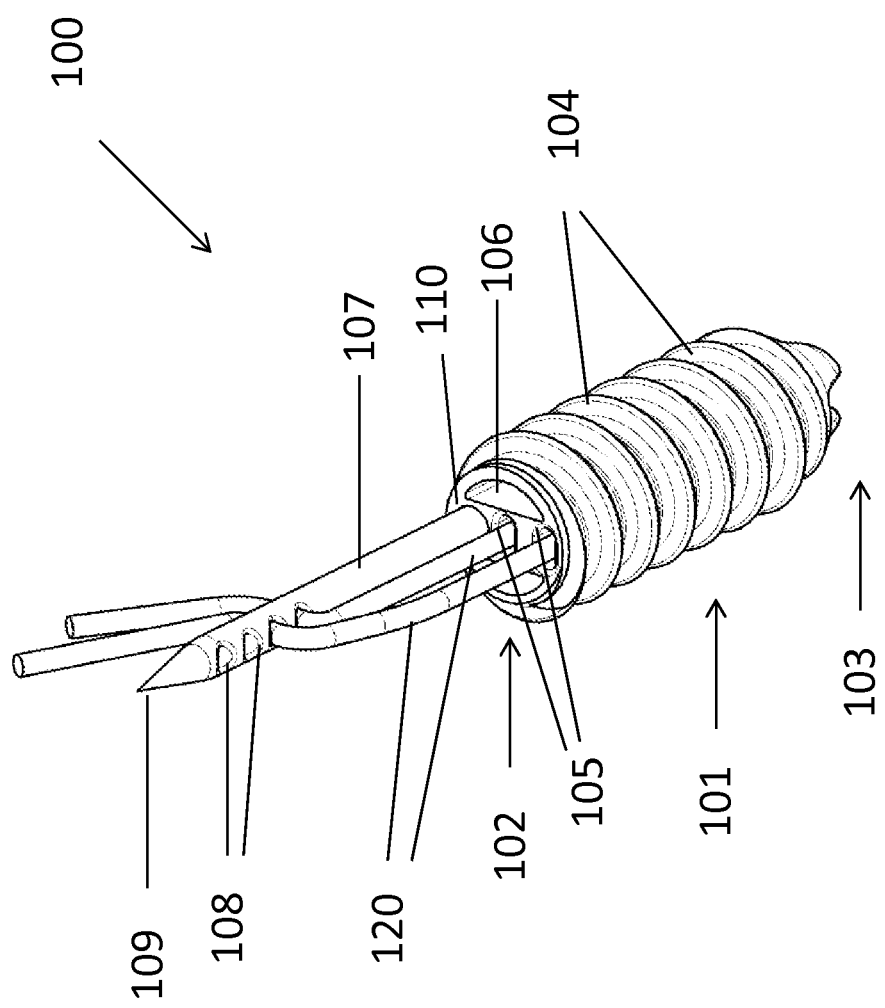
FIG. 1 is a perspective view of an exemplary bone anchor with a pre-loaded needle and suture.
Figure 2:
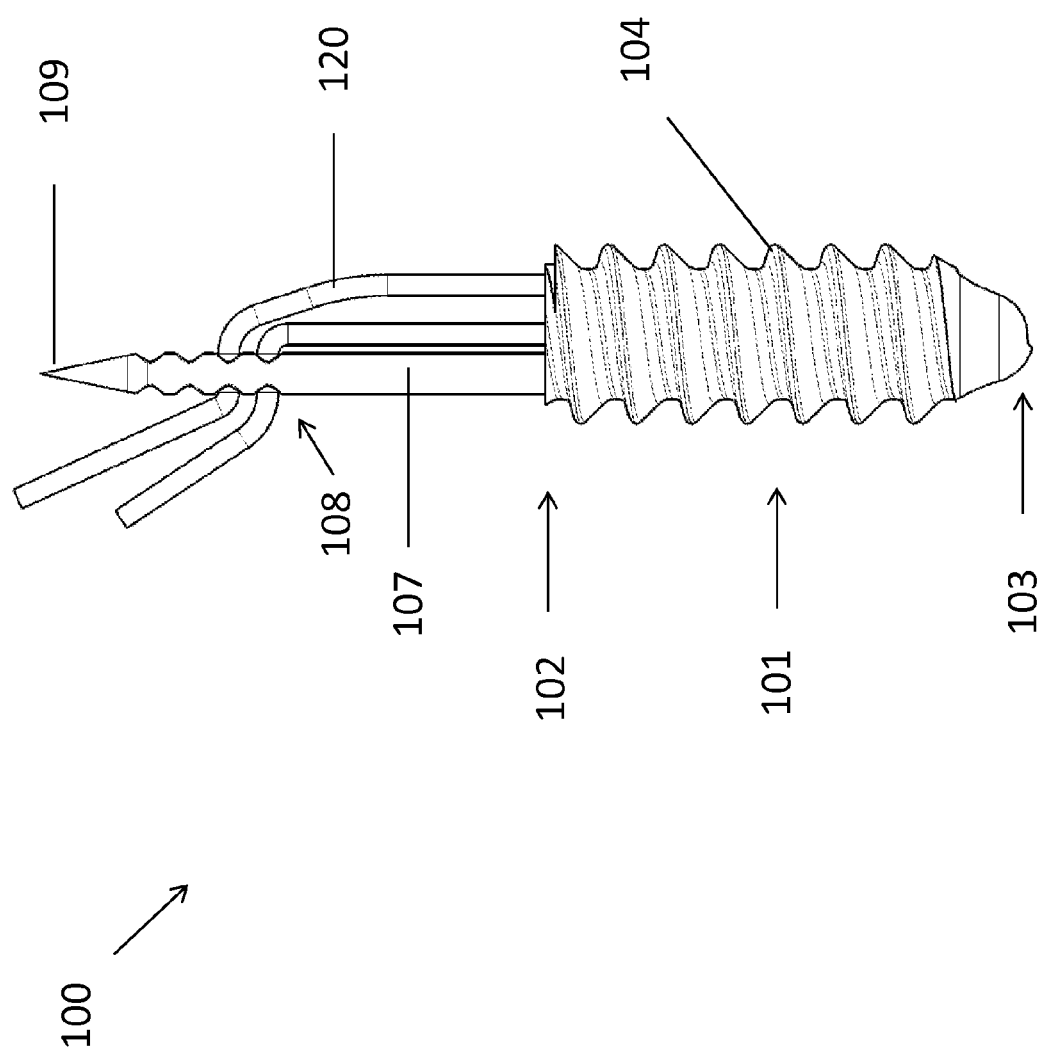
FIG. 2 is a side view of the exemplary bone anchor with a pre-loaded needle and suture of FIG. 1.
Figure 3:
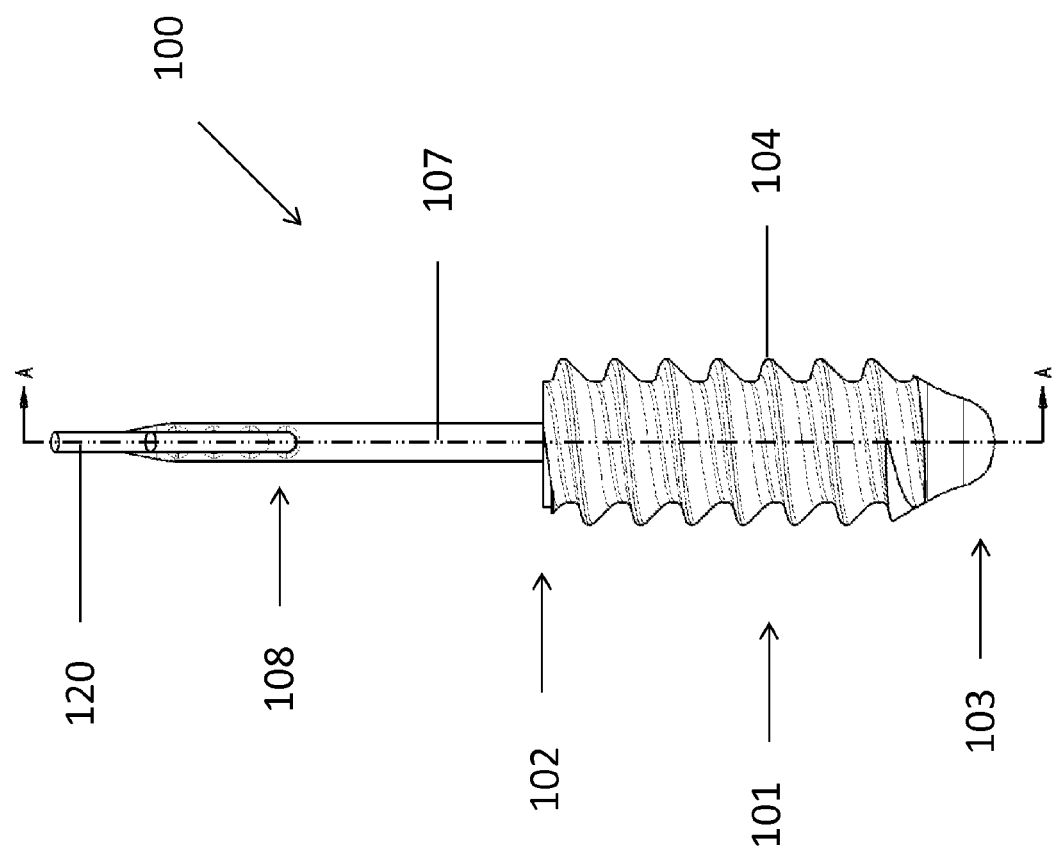
FIG. 3 is a front view of the exemplary bone anchor with a pre-loaded needle and suture of FIG. 1.
Figure 4:
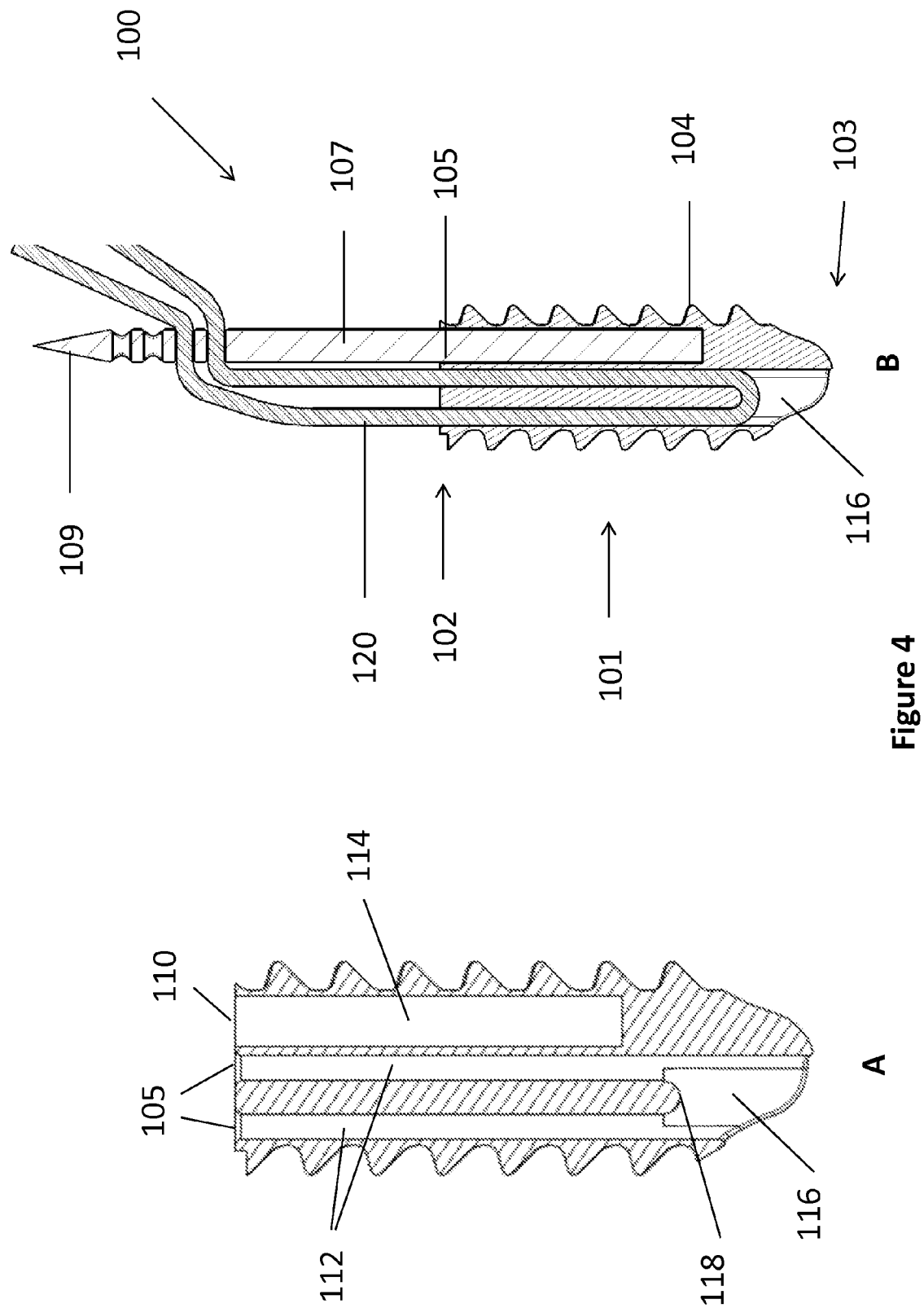
FIG. 4, comprising

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

"Soft tissue" as used herein refers to tissues such as, without limitation, tendons, ligaments, fascia, skin, muscle, fibrous tissues, nerves, blood vessels, synovial membranes and fat.

"Hard tissue" as used herein refers to mineralized tissues, such as bone.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

As used herein, the term "secured," "anchored," "held," "fastened" and similar terms refer to a first component or part being at least temporarily secured, anchored, held, fastened or the like, to a second component or part. In other words, any component described as being secured, anchored, held or fastened to a another component may be either releasably or permanently secured, anchored, held or fastened, unless specifically described otherwise.

Description

The present invention relates to suture or surgical anchors, and methods of attaching soft tissue to hard tissue. Specifically, the present invention relates to a suture anchor for anchoring a soft, second tissue to a hard, first tissue, such as bone, without requiring a surgical instrument or device to pass sutures through the second, soft tissue.

In situations where ligaments or other soft tissue are being sutured to bone, a suture anchor is commonly employed. The suture anchor is inserted into a bore hole in the bone and a suture extending from the anchor is attached to the soft tissue to be secured to the bone. The present invention improves upon this clinical procedure by reducing the amount of steps required for efficient fixation and eliminating the need for additional surgical instrumentation to aid in passing sutures through the soft tissue to be attached.

As described herein, the design of the suture anchor of the present invention significantly reduces the number of traditional steps required to attach soft tissue to bone. The suture anchor is pre-loaded with one or more piercing structures and sutures which allows for easier, faster, and less complex passage of sutures from the bone anchor through the soft tissue.

In one embodiment, the present invention includes a suture anchor for attaching a soft, first tissue to a hard, second tissue. For example, in certain embodiments, the suture anchor is used to attach a soft tissue, including, but not limited to a ligament, tendon, muscle, and the like, to bone. As described herein, the suture anchor of the invention comprises one or more pre-loaded piercing structures which are used to pierce the soft tissue to be attached. In one embodiment, one or more sutures pass through or are attached to the one or more piercing structures. Thus, piercing of the soft tissue with the piercing structure effectively passes the suture through the soft tissue, or permits the piercing structure to be pulled through the soft tissue to effectively pass the suture through the soft tissue, for securing the soft tissue to the hard tissue containing the suture anchor.

As shown in FIGS. 1-4, one embodiment of the suture anchor of the present invention 100 comprises an elongate, anchor body 101 having a proximal face or end 102 and a distal end 103. The proximal end 102 terminates at a proximal face, while the distal end 103 terminates at a distal face or a distal tip. In certain embodiments, the outer surface of the elongate, anchor body 101 comprises a set of projections or flange 104 which, in some instances forms a thread, such as a screw thread used for placing the suture anchor 100 in a hole formed in bone. The spacing of the projections 104 that make up the screw thread may be any suitable spacing known in the art for effective anchoring of the suture anchor 100 in bone. For example, the projections 104 may be helical or non-helical in arrangement. In one embodiment, the projections 104 form one or more continuous helical threads. In one embodiment, anchor body 101 comprises one or more interference fit structures, including but not limited to, ribs, dots, and the like which aid in securing the anchor into bone.

At least a portion of the outer surface of the elongate, anchor body 101 engages a bone, for example through a hole formed in the bone using a bore-forming tool such as a drill, awl, tap, or the like. In one embodiment, the engaging portion of the anchor body 101 extending proximally from the leading distal end 103 is substantially cylindrical, thereby having a substantially constant diameter. In one embodiment, a portion of the elongate, anchor body 101 is tapered. For example, in one embodiment, at least the distal end portion of the body is tapered. In one embodiment, the engaging portion of anchor body 101 has a cylindrical region and a tapered region.

The suture anchor 100 may be manufactured of any suitable biocompatible material known in the art, including, but not limited to titanium, titanium alloys, stainless steel, Nitinol, polyether ether ketone (PEEK), cobalt, alloys thereof, biodegradable polymers, non-degradable polymers, polymeric materials such as non-absorbable polyesters, polyamides, polyolefins, polyurethanes, and polyacetals, homopolymers and copolymers of lactide, glycolide, trimethylene carbonate, caprolactone, and p-dioxanone and blends or and any combinations thereof. In certain embodiments, the suture anchor 100 is made of a bioabsorbable material, thereby allowing it to not be necessary for the anchor to be later removed from the bone. In one embodiment, the suture anchor 100 is made of a non-absorbable material.

Suture anchor 100 may be of any size suitable for the particular application for which it is being used. In one embodiment, the anchor body 101 of suture anchor 100 has a length of about 1 mm to about 200 mm. In one embodiment, the anchor body 101 of suture anchor 100 has a length of about 3 mm to about 100 mm. In one embodiment, the diameter of the anchor body 101 is about 0.1 mm to about 50 mm. In one embodiment, the diameter of the anchor body 101 is about 0.5 mm to about 10 mm.

In one embodiment, the proximal face 102 of the suture anchor 100 comprises at least one recess 106 for engaging an installation tool. For example, the recess 106 may be a depression, cavity or channel having a cross-sectional geometry of a circle, oval, triangle, rectangle, polygon, irregular shape, or the like. The recess 106 is configured to engage a male driver shaft of an installation tool with mating geometry (not shown) to aid in the installation of the suture anchor 100 into a hole in the bone. In one embodiment, instead of a recess, the proximal end 102 of the suture anchor 100 has a geometry which includes a raised or extending feature that allows for engaging of a female driver shaft of an installation tool with mating geometry (not shown). It should be appreciated that the proximal face 102 of suture anchor 100 may include any size and shaped recess and/or extension, such that suture anchor 100 may be engaged by an installation tool to assist in securing suture anchor 100 into the targeted region of bone.

In certain embodiments, the suture anchor 100 comprises one or more piercing structures or needles 107 that extend proximally from the proximal face 102 of the anchor. In one embodiment, the one or more piercing structures 107 is tapered to a form a piercing tip 109 at the leading proximal end of the piercing structure 107, similar to the form of a needle. The piercing tip 109 is used to pierce the targeted soft tissue. The piercing structure 107 may be of any length extending from the proximal face 102 of the anchor body 101. For example, the length of the piercing structure 107 extending from the proximal face of the body is any suitable length that transverses the entirety of the thickness of the soft tissue being secured to bone. In one embodiment, the length of the piercing structure 107 extending from the proximal face of the body is about 1 mm to about 50 mm. In certain embodiments, the piercing structure 107 has a first region having a constant diameter and a second region, located at or near piercing tip 109, which has a tapered diameter. In certain embodiments, the surface along the length of piercing structure 107 may be smooth, or it may include one or more structures, such as ridges, recesses, or combinations thereof, as desired. The piercing structure may be manufactured of the same types of materials identified above for the anchor body. Preferably, the piercing structure is composed of titanium or stainless steel.

In one embodiment, at least a portion of the distal end of the piercing structure 107 is embedded within the anchor body 101. For example, as seen in FIGS. 4A and 4B, the proximal face 102 of anchor body 101 includes an opening 110 to a cavity 114 extending from the proximal face 102 into at least a portion of the body 101, where the distal end of the piercing structure 107 is configured to fit into the cavity 114. In one embodiment, the cavity 114 has a step or gradual change in diameter which secures piercing structure 107 within cavity 114 at a desired depth within cavity 114. In one embodiment, the at least one piercing structure 107 is removable, such that the piercing structure 107 can be pulled out or otherwise released from cavity 114. In such embodiments, piercing structure 107 and cavity 114 may include any sort of temporary securing system known in the art, such as a detent or friction fit mechanism, to permit piercing structure 107 to be secured within the cavity 114 while the anchor body 101 is secured to bone and while the soft tissue is punctured, and then subsequently released from the cavity 114 with the application of a light, pulling force.

In one embodiment, piercing structure 107 is permanently affixed to body 101 of the suture anchor 100. For example, in one embodiment, the suture anchor 100 is a unitary piece which comprises the features of the anchor body 101 and the piercing structure 107, such that the piercing structure 107 is integrated with the body 101 of the anchor 100.

The piercing structures 107 may have any cross-sectional geometry, including, circular, or polygon shaped. In one embodiment, piercing structure 107 and the cavity 114 have a mating geometry such that piercing structure 107 cannot rotate freely within cavity 114. In certain embodiments, piercing structure 107 is designed to mate with an installation tool to aid in the securing of anchor 100 into bone. For example, in one embodiment, piercing structure 107 has a size and shape which engages an installation tool. In one embodiment, piercing structure 107 comprises a tool engaging element which engages an installation tool. This allows for the installation to act upon the piercing structure in order to drive anchor 100 into bone. That is, the installation tool engages piercing structure 107 and applies force or torque to piercing structure 107 in order to drive anchor 100 into bone.

The one or more piercing structures 107 may be arranged in any manner. For example, in one embodiment, the one or more piercing structures 107 may be positioned along an outer circumference of the proximal face 102. In another embodiment, the one or more piercing structures 107 may be positioned at the center of the proximal face 102. In one embodiment, two or more piercing structures 107 are positioned equidistant from each other. In one embodiment, the one or more piercing structures 107 comprise a mechanical holder that retains the distance between two or more piercing structures 107 to a relatively small distance. In certain embodiments, the mechanical holder can be removed between the piercing structures 107 to relatively increase the distance between the preloaded piercing structures 107.

In one embodiment, the one or more piercing structures 107 have different lengths, allowing the different piercing structures 107 to penetrate through the soft tissue to different distances. In certain embodiments, the one or more piercing structures 107 comprise a crimping instrument, which crimps the soft tissue prior to the piercing of the soft tissue.

The one or more piercing structures 107 comprise one or more engagement structures 108 for engaging one or more sutures 120. Exemplary engagement structures 108 may be, without limitation, a hole, crimp, notch, or the like. For example, as depicted in FIGS. 1-4, the piercing structure 107 comprises at least a first and second hole 108, each hole traversing the piercing structure 107. Each hole 108 is configured to engage at least a portion of a suture 120, such that the suture 120 passes through the piercing structure 107. For example, in one embodiment, anchor 100 comprises at least one suture 120, wherein a first portion of suture 120 engages the first hole in piercing structure 107 and a second portion of suture 120 engages the second hole in piercing structure 107. In one embodiment, piercing structure 107 comprises only one hole, wherein the first and second portions of suture 120 both engage the single hole. In this way, both ends of the suture 120 are passed through the piercing structure 107 of the anchor 100. It should be understood that engagement structure 108 for engaging at least one suture 120 is not limited to a hole in piercing structure 107. Rather, any engagement structure 108 that engages suture 120 to allow passage of suture 120 and/or securing of suture 120 to piercing structure 107 may be used. For example, in one embodiment, piercing structure 107 comprises one or more notches or crimped regions, where a portion of suture 120 engages the notch to secure suture 120. In one embodiment, piercing structure 107 comprises one or more adhesive regions, where a portion of suture 120 engages the adhesive region to secure suture 120. In another embodiment, piercing structure 107 is cannulated, allowing for a suture 120 to enter and pass through at least a portion of the cannulated interior of piercing structure 107.

In certain embodiments, as is shown in FIGS. 1-4, while a first portion and second portion of suture 120 are engaged with piercing structure 107, the region between the first portion and second portion is held or secured on or within anchor body 101 of the anchor 100. For example, as shown in FIGS. 4A and 4B, the anchor body 101 comprises two openings 105, each leading to a suture channel 112 that opens to a cavity 116 at the distal end 103 of anchor body 101. In one embodiment, distal end 103 comprises an opening located at or near the tip which opens into cavity 116.

In certain embodiments, suture 120 is looped through channels 112, such that the suture 120 is secured against a partition 118 within cavity 116. In certain embodiments, partition 118 may be protrude into cavity 116 with a curved surface, such that suture 120 is secured against partition 118 when pulled taut. In other embodiments, partition 118 does not protrude into cavity 118. In one embodiment, suture channels 112 are entirely comprised within anchor body 101. In another embodiment, at least a portion of suture channels 112 are open, wherein at least a portion of suture channels 112 extend along the outer surface of anchor body 101. It should be appreciated that suture channels 112 may be substantially straight and parallel to one another, or they may be arched or serpentine. The cross-sectional geometry of suture channels 112 may be circular, or polygon shaped, and are configured for the general passage of a suture 120. For example, the diameter, or other cross-sectional dimension of suture channels 112 are equal to or greater than the diameter of suture 120. Suture channels 112 and the one or more suture engagement structures 108 positioned along the at least one piercing structure 107 hold suture 120 within the anchor 100. In certain embodiments, the suture 120, when loaded into the anchor 100, is free to move (e.g., slide or slip) within the suture channels 112 and cavity 116. In another embodiment, the suture 120, when loaded into the anchor 100, is substantially non-movable, thereby securing the suture 120 to the anchor 100. It should also be appreciated that anchor 100 may include multiple suture channel 112 pairs leading to one or more cavities 116, such that multiple sutures 120 may be pre-loaded with one or more piercing structures 107, such that each suture 120 may be individually utilized during a surgical procedure.

Figure 5:
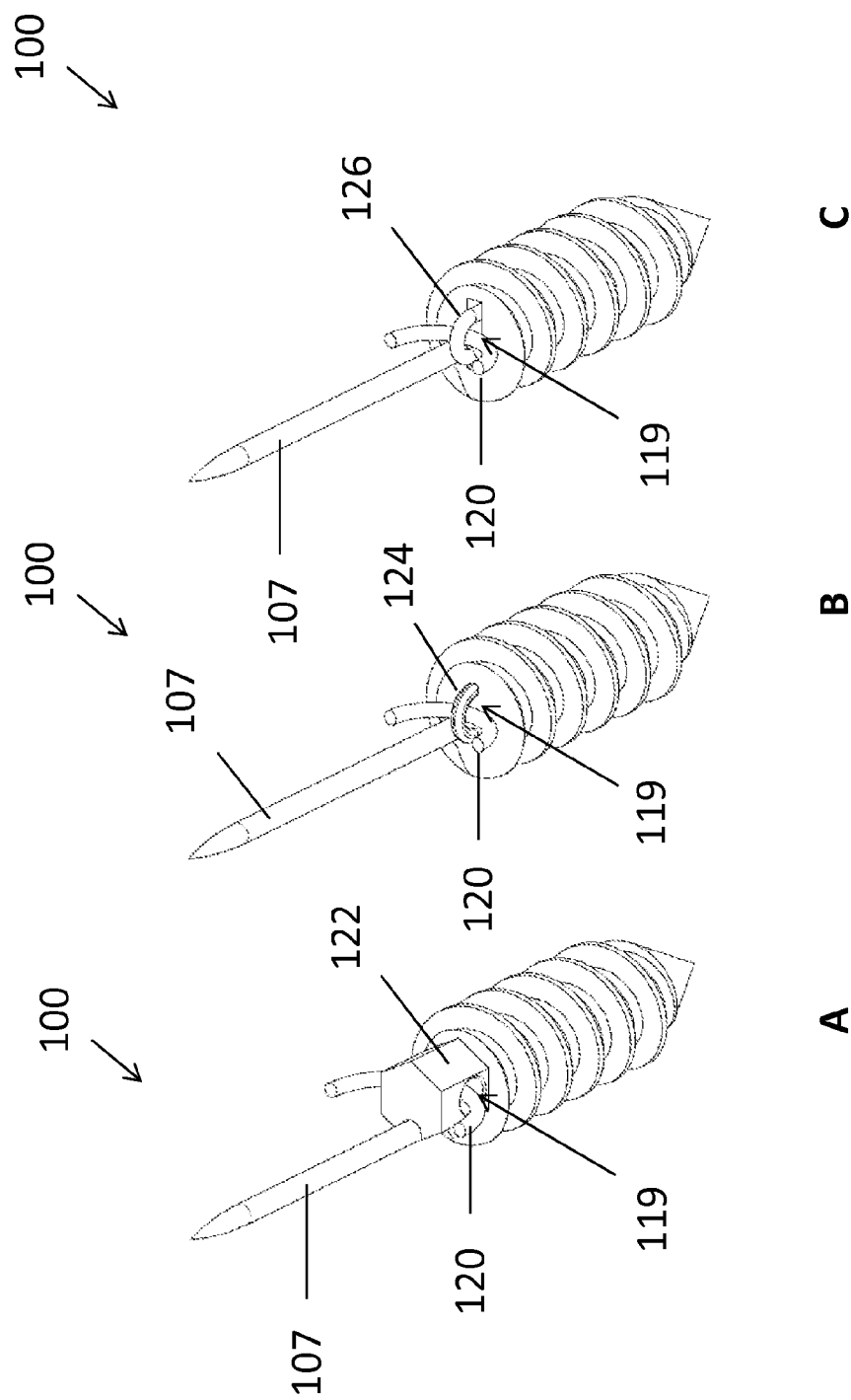
FIG. 5, comprising

It should be appreciated that the present invention is not limited to the suture held within the body using suture channels. Rather, the present invention encompasses the use of an eyelet, groove, cross-hole, or other mechanism for holding a suture within the anchor body. For example, as shown in FIGS. 5A-5C, anchor 100 may include an extension block 122 having a hole 119 therethrough (FIG. 5A), an extended eyelet structure 124 having a hole 119 therethrough, or a cinching structure 126 having a hole 119 therethrough, that cinches down onto suture 120.

In certain embodiments, the anchor comprises more than one suture 120. For example, in one embodiment, more than one suture 120 is positioned within suture channels 112. In one embodiment, the anchor 100 comprises more than one suture channel pair, each with one or more sutures 120 positioned therein. The one or more sutures 120 may engage the at least one piercing structure 107 at the same, or at different engagement structures 108. For example, in one embodiment, one or more sutures 120 pass through the same holes 108 in the piercing structure 107. In one embodiment, each suture 120 passes through its own hole 108 in the piercing structure 107. In one embodiment, each suture 120 passes through a different piercing structure 107.

The suture of the anchor of the present invention may be any suture known in the art suitable for the particular application. Exemplary sutures include sutures made from materials including, but not limited to, catgut, silk, linen, nylon, polyglycolic acid, polyglactin, polydioxone, polyglyconate, polyamide, polyester, polypropylene, polyethylene and ultra-high molecular weight polyethylene.

Figure 6:
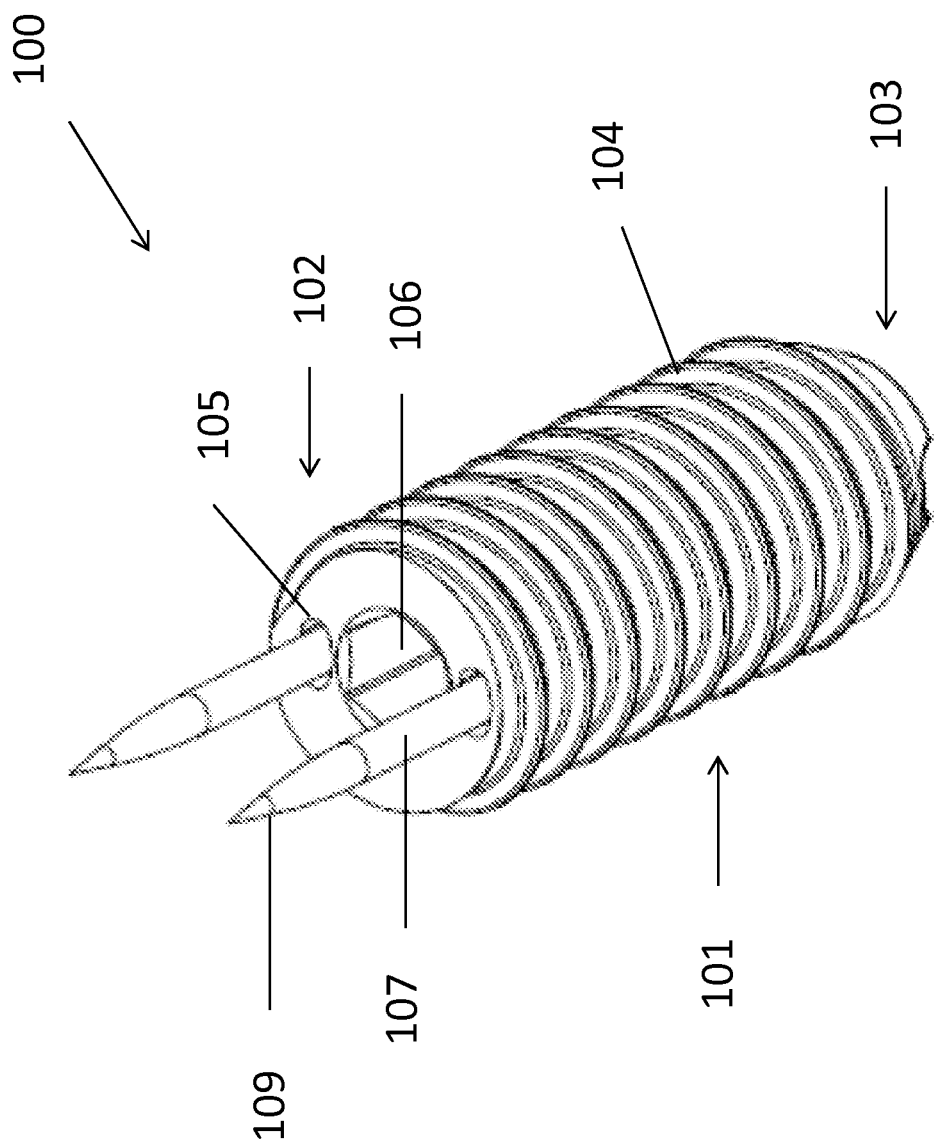
FIG. 6 is a perspective view of another exemplary bone anchor with a pre-loaded needle and suture.
Figure 7:
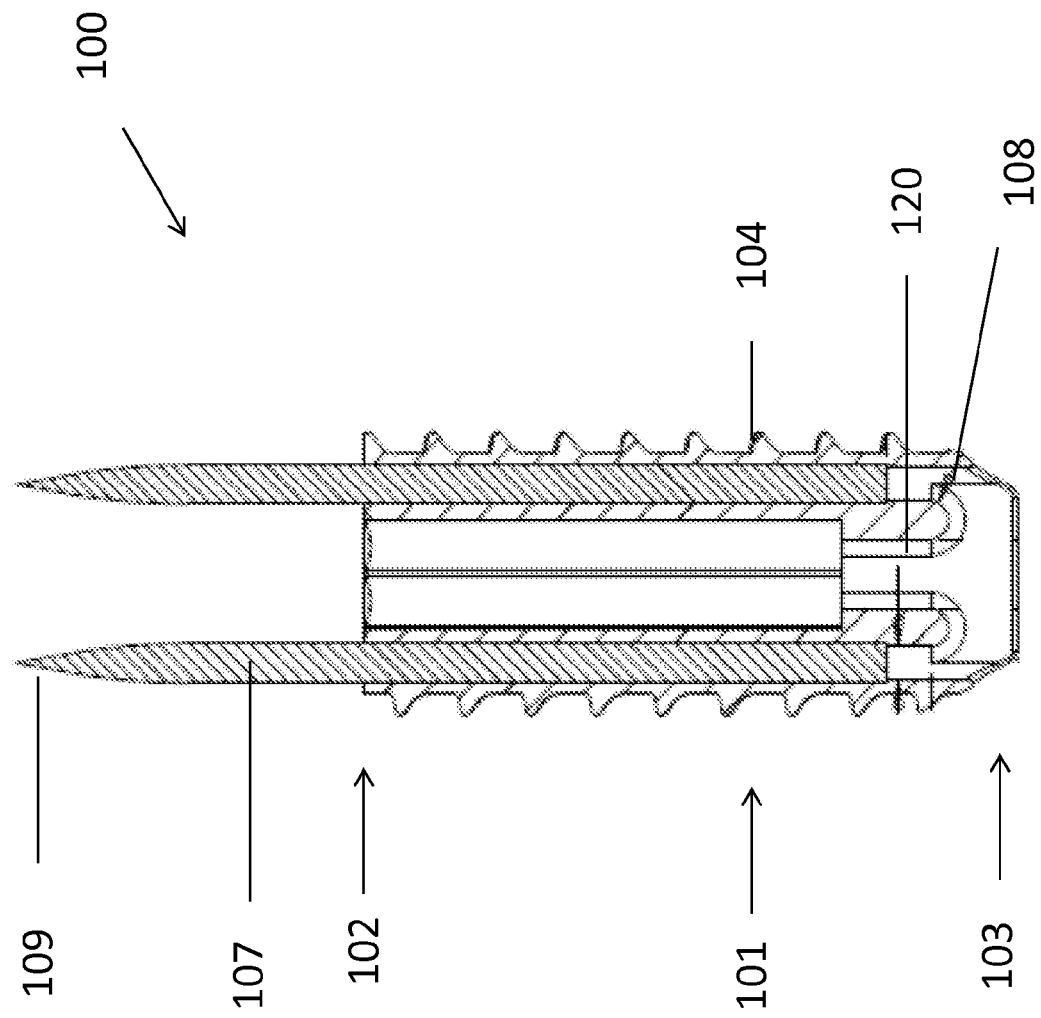
FIG. 7 is a cross-sectional view of the exemplary bone anchor with a pre-loaded needle and suture of FIG. 6.

As contemplated herein, the present invention may include alternative embodiments of the anchor 100. For example, as shown in FIGS. 6 and 7, the anchor 100 may include multiple piercing structures 107 having a leading, piercing tip 109 at their proximal ends, while each being connected to at least one suture 120 at their distal ends via any sort of suture engagement structure, respectively. In this embodiment, removal of piercing structure 107 from anchor 100 pulls pre-attached suture 120 out of anchor 100 as well. Thus, once piercing structure 107 pierces the soft tissue and is removed, suture 120 is passed through the soft tissue. It should be appreciated that the anchors 100 of the present invention may be designed in any desired configuration, provided the anchor includes at least one pre-loaded piercing structure and suture associated with the anchor body.

The present invention also includes a method of anchoring a soft tissue to bone. The method may be used for any reconstructive or orthopedic clinical application, including the fastening of ligaments, tendons, muscles, and the like to bone. The method may be used for the repair and reattachment of damaged soft tissue in the shoulder, elbow, wrist, hip, knee, ankle, jaw, and the like.

In certain embodiments, the method comprises securing the bone anchor, described elsewhere herein, into the bone to which the soft tissue is being attached. In one embodiment, the bone anchor is secured into a pre-formed bore in the bone, which may be formed using a bone-forming tool such as an awl, tap, drill, or the like. In another embodiment, the bone anchor is self-tapped or self-drilled into the bone. In certain embodiments, the method comprises using an installation tool, wherein a driver shaft engages a portion of the anchor. In one embodiment, the installation tool engages a portion of the body. In one embodiment, the installation tool engages a piercing structure of the anchor.

Once the anchor body has been secured to the bone, the method comprises administering the soft tissue over the proximal face of the anchor body, such that the one or more piercing structures, pre-loaded with one or more sutures, pierce the soft tissue. In certain embodiments, the one or more piercing structures of the anchor are advanced through the soft tissue such that the attached sutures pass through the entirety of the tissue, and are thus accessible from the top surface of the tissue. In another embodiment, the one or more piercing structures of the anchor are advanced through the soft tissue and pulled out of the anchor body and through the soft tissue, such that the attached sutures pass through the entirety of the soft tissue, and are thus accessible from the top surface of the soft tissue. In another embodiment, a first region of the soft tissue is pushed overtop the one or more piercing structures of the anchor to advance the piercing structure through the soft tissue to allow a first suture or sutures to pass through the entirety of the soft tissue at the first region. Then, the soft tissue is lifted off the one or more piercing structures, so that the process can be repeated at a second region of the soft tissue. In this manner, the same anchor can be used to secure the soft tissue at any number of desired regions along the soft tissue. In one embodiment, the method comprises advancing a suture retriever to the anchored soft tissue to pull the one or more sutures from the piercing structure. The suture ends may then be tied together to form a knot. In certain embodiments, the formed knot is pushed to the top surface of soft tissue, thereby fixing the soft tissue to the bone. In certain embodiments, after the one or more piercing structures pierce the tissue, the one or more piercing structures are pulled out of, or otherwise released from, the anchor device. In certain instances, pulling of the one or more piercing structures pulls out the attached sutures from the piercing structures.

In certain embodiments, the method comprises using one or more of the anchors of the invention for fixation of the soft tissue at one or more locations along the bone. The number and spacing of the anchors may be varied depending on the particular application and extent of the injury.

In certain embodiments, the method of tying down soft tissue to bone using the present invention comprises the steps of: 1) boring out the bone; 2) securing the suture anchor with pre-loaded piercing structures into the bone bore; 3) pulling the soft tissue over the suture anchor such that the pre-loaded piercing structure pierces the soft tissue and at least a portion of the pre-loaded suture is exposed above the pierced soft tissue surface; and 4) tying the suture into a knot against the soft tissue surface to secure the soft tissue to bone.

In certain embodiments, a portion of the piercing structure pierces the soft tissue, and the piercing structure is removed from the anchor, which results in the passage of the suture, which is attached to the piercing structure, through the soft tissue. For example, in certain embodiments, the method of tying down soft tissue to bone using the present invention may comprise: 1) boring out the bone; 2) securing the suture anchor with pre-loaded piercing structures into the bone bore; 3) pulling the soft tissue over the suture anchor such that the pre-loaded piercing structure pierces the soft tissue; 4) pulling the piercing structure and pre-loaded suture out of the bone anchor body, pulling with it the pre-attached sutures; and 5) tying the suture into a knot against the soft tissue surface to secure the soft tissue to bone.

The present invention includes a system for securing soft tissue to bone. In one embodiment, the system comprises at least one anchor comprising at least one piercing structure and at least one suture secured to the anchor and engaged with the at least one piercing structure. In one embodiment, the system comprises an installation tool which engages at least a portion of the anchor to drive the anchor into bone. For example, the installation tool may comprise a male driver shaft with a particular geometry to engage a structure or recess of the anchor. In one embodiment, the installation tool may comprise a female driver shaft which engages the proximal end of the anchor. In one embodiment, the installation tool engages the piercing structure of the anchor in order to drive the anchor into the bone. In certain embodiments, the system comprises a suture retriever used to remove an engaged suture from a piercing structure after the piercing structure has pierced the soft tissue. The system may comprise one or more surgical instruments for manipulating the soft tissue or bone or to form a knot using the passed sutures.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of attaching soft tissue to bone in a subject comprising the steps of:
   securing a suture anchor into the bone, the suture anchor comprising an anchor body, at least one piercing structure in direct contact with and extending from the anchor body, and at least one suture, wherein the at least one suture is secured to the anchor body and engages the at least one piercing structure;

piercing a soft tissue by forcing the at least one piercing structure through the soft tissue while the at least one piercing structure remains in direct contact with the anchor, such that at least a portion of the at least one suture passes through the soft tissue; and tying the at least one suture against the soft tissue to secure the soft tissue to the bone;

further comprising releasing at least one suture from the at least one piercing structure;

lifting the soft tissue off of the anchor body; and piercing a second portion of the soft tissue by forcing the at least one piercing structure through the second portion of the soft tissue.

2. The method of claim 1, wherein the suture anchor is secured into the bone through self-drilling.

3. The method of claim 1, wherein the suture anchor is secured into the bone by forming a bore in the bone using a bore-forming tool, and securing the suture anchor into the bore.

4. The method of claim 1, wherein the soft tissue is selected from the group consisting of tendon, muscle, and ligament.

5. The method of claim 1, wherein the suture anchor is secured into the bone using an installation tool which engages a structure of the anchor body.

6. The method of claim 1, wherein the suture anchor is secured into the bone using an installation tool which engages the at least one piercing structure.

7. The method of claim 1, further comprising releasing the at least one piercing structure from the anchor body.

\* \* \* \* \*